United States Patent
Sitnitsky et al.

(10) Patent No.: US 12,150,893 B2
(45) Date of Patent: Nov. 26, 2024

(54) ROBOTIC MOVEMENT FOR VISION CARE SURGERY MIMICKING PROBE NAVIGATED BY MAGNETIC TRACKING

(71) Applicant: JOHNSON & JOHNSON SURGICAL VISION, INC., Irvine, CA (US)

(72) Inventors: Ilya Sitnitsky, Nahariya (IL); Vadim Gliner, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 431 days.

(21) Appl. No.: 17/501,679

(22) Filed: Oct. 14, 2021

(65) Prior Publication Data
US 2023/0117302 A1 Apr. 20, 2023

(51) Int. Cl.
| | |
|---|---|
| A61F 9/007 | (2006.01) |
| A61B 34/00 | (2016.01) |
| A61B 34/20 | (2016.01) |
| A61B 34/37 | (2016.01) |

(52) U.S. Cl.
CPC .......... *A61F 9/00736* (2013.01); *A61B 34/20* (2016.02); *A61B 34/37* (2016.02); *A61B 34/77* (2016.02); *A61B 2034/2072* (2016.02)

(58) Field of Classification Search
CPC ..... A61F 9/00736; A61B 34/20; A61B 34/37; A61B 34/77; A61B 2034/2072
USPC ............................................................ 606/1
See application file for complete search history.

(56) References Cited

U.S. PATENT DOCUMENTS

| | | | |
|---|---|---|---|
| 5,391,199 A | 2/1995 | Ben-Haim | |
| 6,120,433 A * | 9/2000 | Mizuno | A61B 34/76 600/102 |
| 6,239,724 B1 | 5/2001 | Doron et al. | |
| 6,332,089 B1 | 12/2001 | Acker et al. | |
| 6,484,118 B1 | 11/2002 | Govari | |

(Continued)

FOREIGN PATENT DOCUMENTS

WO 1996005768 A1 2/1996

OTHER PUBLICATIONS

Ahronovich E.Z., et al., "A Review of Robotic and OCT-Aided Systems for Vitreoretinal Surgery," Advances in Therapy, Apr. 2021, vol. 38 (5), pp. 2114-2129, XP037447793, DOI: 10.1007/s12325-021-01692-z, ISSN: 0741-238X, [retrieved on Apr. 3, 2021].

(Continued)

*Primary Examiner* — Michael J Lau

(57) ABSTRACT

An eye surgery apparatus includes a model surgical tool, a robotic arm coupled with an eye surgery tool, a tracking-system, and a processor. The model surgical tool is configured to be maneuvered by a physician. The robotic arm is coupled with an eye surgery tool and configured to be placed in proximity to an eye of a patient. The tracking-system is configured to track movements of at least the model surgical tool. The processor is configured to (i) receive the tracked movements of the model surgical tool from the tracking system, while the physician moves the model surgical tool to perform a model eye surgery on an oversized model eye, and (ii) apply to the robotic arm movements that mirror and scale-down the movements applied by the physician to the model surgical tool, to perform a surgical procedure on the eye of the patient using the eye surgery tool.

26 Claims, 3 Drawing Sheets

(56) References Cited

U.S. PATENT DOCUMENTS

| | | |
|---|---|---|
| 6,618,612 B1 | 9/2003 | Acker et al. |
| 6,690,963 B2 | 2/2004 | Ben-Haim et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2006/0241414 A1 | 10/2006 | Nowlin et al. |
| 2013/0131867 A1 | 5/2013 | Olds et al. |
| 2015/0335480 A1* | 11/2015 | Alvarez ............... A61B 5/0059 606/130 |
| 2019/0051216 A1* | 2/2019 | Bernal ................... G16H 40/40 |
| 2019/0336222 A1* | 11/2019 | Schneider .............. A61B 34/20 |
| 2020/0022775 A1* | 1/2020 | Garcia Kilroy ........ A61B 90/37 |
| 2020/0197114 A1* | 6/2020 | Cunningham .......... A61B 34/76 |
| 2020/0405403 A1 | 12/2020 | Shelton et al. |
| 2021/0196417 A1* | 7/2021 | Simi ...................... A61B 34/35 |

OTHER PUBLICATIONS

Rahimy et al. Robot-assisted intraocular surgery: development of the IRISS and feasibility studies in an animal model. Eye (Lond). Aug. 2013;27(8):972-8. doi: 10.1038/eye.2013.105. Epub May 31, 2013. PMID: 23722720; PMCID: PMC3740307.

Berkelman et al. A Compact Modular Teleoperated Robotic System for Laparoscopic Surgery. Int J Rob Res. 2009;28(9):1198-1215. doi:10.1177/0278364909104276.

Van Mulken et al. "Robotic (super) microsurgery: Feasibility of a new master-slave platform in an in vivo animal model and future directions." Journal of surgical oncology vol. 118,5 (2018): 826-831. doi:10.1002/jso.25195.

Pandey et al. Robotics and ophthalmology: Are we there yet? Indian J Ophthalmol. Jul. 2019;67(7):988-994. doi:10.4103/ijo.IJO_1131_18. PMID: 31238393; PMCID: PMC6611303.

* cited by examiner

ROBOTIC MOVEMENT FOR VISION CARE SURGERY MIMICKING PROBE NAVIGATED BY MAGNETIC TRACKING

FIELD OF THE INVENTION

The present invention relates generally to robotic medical systems for eye surgery, and particularly to mimicking robotic eye surgery systems.

BACKGROUND OF THE INVENTION

Various techniques to perform a surgery using robotic systems were proposed in the patent literature. For example, U.S. Patent Application Publication 2006/0241414 describes robotic surgical systems which allow selectable independent repositioning of an input handle of a master controller and/or a surgical end effector without corresponding movement of the other. In some embodiments, independent repositioning is limited to translational degrees of freedom. In other embodiments, the system provides an input device adjacent a manipulator supporting the surgical instrument so that an assistant can reposition the instrument at the patient's side.

As another example, U.S. Patent Application Publication 2020/0405403 describes a method of using a surgical modular robotic assembly including an interchangeable motor pack, a hand-held surgical instrument, and a robotic surgical instrument. The method includes releasably attaching an interface portion of the interchangeable motor pack to the hand-held surgical instrument, causing the interchangeable motor pack to drive a first surgical tool of the hand-held surgical instrument, stopping the interchangeable motor pack from driving the first surgical tool, disconnecting the interface portion from the hand-held surgical instrument, and releasably attaching the interface portion of the interchangeable motor pack to the robotic surgical instrument.

SUMMARY OF THE INVENTION

An embodiment of the present invention that is described hereinafter provides an eye surgery apparatus including a model surgical tool, a robotic arm coupled with an eye surgery tool, a tracking system, and a processor. The model surgical tool is configured to be maneuvered by a physician. The robotic arm is coupled with an eye surgery tool and configured to be placed in proximity to an eye of a patient. The tracking system is configured to track movements of at least the model surgical tool. The processor is configured to (i) receive the tracked movements of the model surgical tool from the tracking system, while the physician moves the model surgical tool to perform a model eye surgery on an oversized model eye, and (ii) apply to the robotic arm movements that mirror and scale-down the movements applied by the physician to the model surgical tool, so as to perform a surgical procedure on the eye of the patient using the eye surgery tool.

In some embodiments, the eye surgery apparatus further includes an additional robotic arm that is configured to hold the model surgical tool and to be maneuvered by the physician. In an embodiment, the additional robotic arm is mechanically loose, so as to be maneuverable by the physician.

In some embodiments, the model surgical tool is manually held in space by the physician.

In some embodiments, the eye surgery apparatus further includes a magnetic position-tracking sensor for the eye surgery tool, and wherein the tracking system is further configured to track the movements of the eye surgery tool by tracking the magnetic position-tracking sensor. In an embodiment, the tracking system is further configured to track the movements of the model surgical tool by tracking a second magnetic position-tracking sensor used for the model surgical tool.

In some embodiments, the eye surgery apparatus further includes a magnetic position-tracking sensor for the model surgical tool, and wherein the tracking system is configured to track the movements of the model surgical tool by tracking the magnetic position-tracking sensor. In an embodiment, the magnetic position-tracking sensor includes one selected from the group consisting of a dual-axis sensor (DAS) and a triple-axis sensor (TAS).

In some embodiments, the tracking system includes a magnetic tracking system including a pad, which includes magnetic-field generators and is placed in a vicinity of the patient.

In some embodiments, the eye surgery tool is a phacoemulsification probe.

In an embodiment, the eye surgery apparatus further includes an additional robotic arm coupled with an additional eye surgery tool, wherein the additional robotic arm is configured to have the additional eye surgery tool mimicking an additional model surgery tool. In another embodiment, the additional eye surgery tool is configured to move lens material in the eye.

In some embodiments, the oversized model eye is projected with a 3D image of the eye of the patient, the image provided in real time.

There is additionally provided, in accordance with another embodiment of the present invention, an eye surgery method including maneuvering a model surgical tool by a physician. A robotic arm coupled with an eye surgery tool is placed in proximity to an eye of a patient. Using a tracking system, movements are tracked of at least the model surgical tool. The tracked movements of the model surgical tool are received from the tracking system, while the physician moves the model surgical tool to perform a model eye surgery on an oversized model eye. Movements are applied to the robotic arm, that mirror and scale-down the movements applied by the physician to the model surgical tool, so as to perform a surgical procedure on the eye of the patient using the eye surgery tool.

The present invention will be more fully understood from the following detailed description of the embodiments thereof, taken together with the drawings in which:

DETAILED DESCRIPTION OF EMBODIMENTS

Overview

Figure 1:
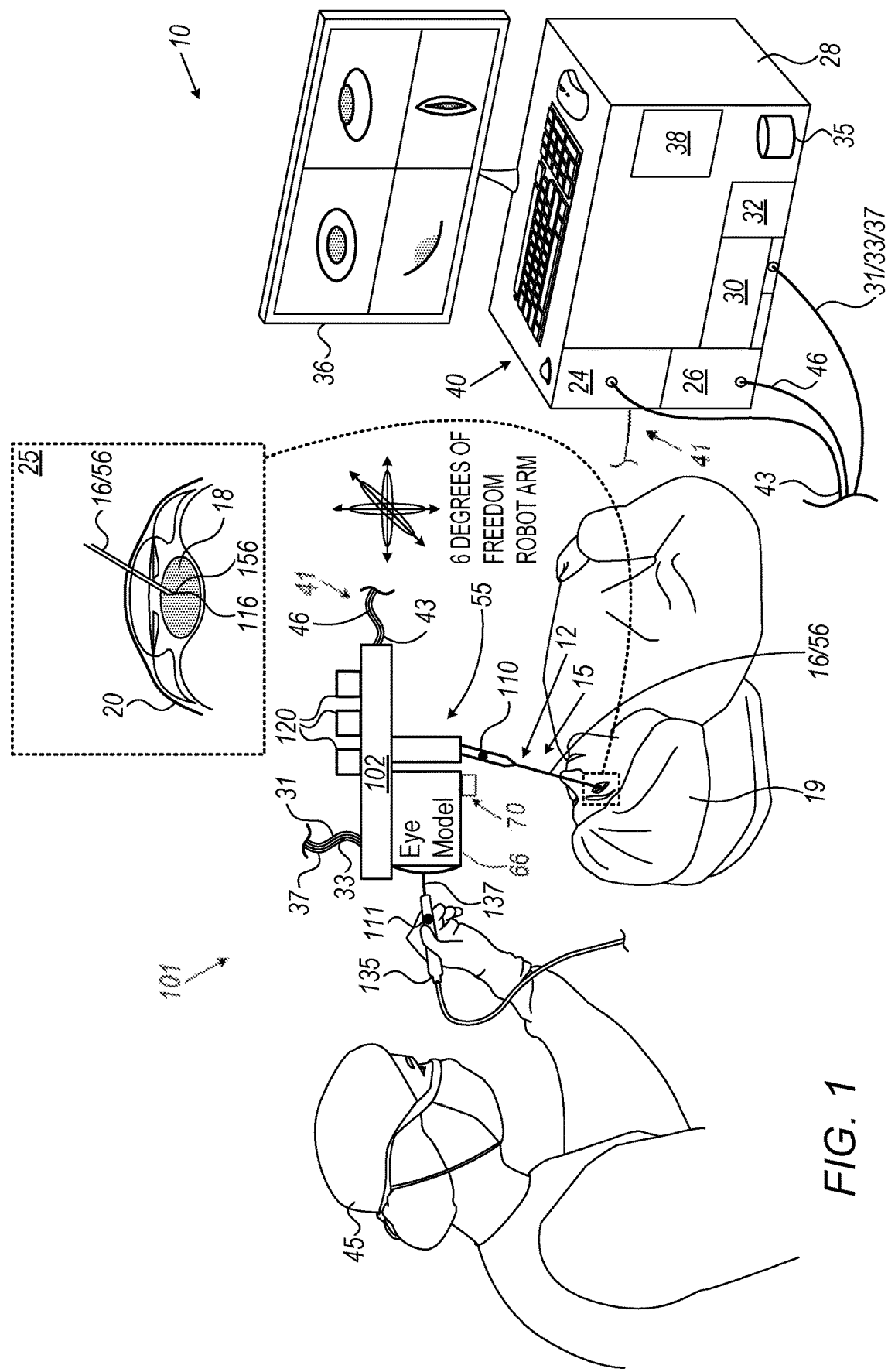
FIG. 1 is a schematic, pictorial view of a robotic phacoemulsification apparatus comprising a robotically held position-trackable mimicking phacoemulsification probe, in accordance with an embodiment of the present invention.

Eye surgery, such as cataract surgery (e.g., phacoemulsification), is a delicate procedure, and even an experienced physician must conduct it very cautiously. In particular, eye surgery involves operating one or more tools (e.g., probes) in a very compact and complex region of an eye, and therefore the physician is required to minutely manipulate any surgical probe inserted therein.

Embodiments of the present invention that are described hereinafter provide systems and methods for robotic eye surgery using a surgical robot that performs the actual surgery by mimicking motions and actions of a model surgical tool used by a physician to perform a simulated operation on an enlarged eye model. Using the magnification ratio between the model and the actual eye, together with the mimicking robot's accuracy, allows the performance of highly accurate and safe eye surgery.

In particular, the disclosed systems and method are designed to facilitate surgery using a minimally invasive approach for the eye surgery (e.g., cataract surgery) with a limited incision in the eye through which a probe is inserted and maneuvered without further damaging the cut tissue boundaries.

In an example embodiment, during cataract surgery, a robotic arm follows a model surgical tool coupled to a mechanically loose robotic arm of a two-arm robot. In the context of the present patent application and in the claims, the term "loose arm" or "loosened arm" refers to a robotic arm that is not actively driven by any automated means, but rather intended to be maneuvered by a human user in order to track and mimic the arm's movements.

The physician moves the loose arm to perform a mock emulsification procedure on a lens of enlarged eye model. In the process, a genuine phacoemulsification probe coupled to the second, mimicking, arm of the robot emulsifies a lens of a real eye. The emulsified particles of the real eye are aspirated, and replenishment fluid is irrigated therein by the surgical robotically held probe.

In an embodiment, a 3D image of the actual patient eye is projected onto the eye model in real time. The projection enables the physician viewing the eye model to direct the tool at particles that need to be emulsified, for example. The physician may occasionally verify the observation by inspecting the patient eye through a dedicated microscope.

In one embodiment described herein, such a two-arm robot (or two separate robotic arms which are registered with each other) has one arm loosened so that it can be maneuvered by the physician. The loosened arm holds a model surgical tool (e.g., a model phacoemulsification probe). The second robotic arm holds a real eye surgery tool (e.g., a phacoemulsification probe) and is placed in proximity to the eye of a patient. To facilitate independent (i.e., with feedback not from the robot itself only) closed loop control, the movements of the model tool and/or eye surgery tool are tracked using a magnetic location-tracking system, or using another tracking method such as be optically tracked. The tracking-system typically comprises a location pad placed in the vicinity of the patient, assuming that the head is secured, around the neck of the patient, or placed around the patient's head. The coordinate systems of the patient, the robot and the magnetic location-tracking system are registered with one another.

The physician moves the model tool in the loosened arm to perform an imitated eye surgery (e.g., cataract surgery) procedure on the oversized model eye. The movements of the loosened arm are tracked by a controller and mirrored (while scaling down the movements) to the second robotic arm which holds the real eye surgery tool and performs, using the eye surgery tool, the surgical procedure on the eye of the patient based on the movements of the physician. In this way large movements of the physician may be translated to small movements of the probe to perform a very accurate cataract procedure.

Such an accurately registered and magnified motion of the loose robotic arm allows for accurate location and direction of the eye surgery tool. For example, it allows accurately registered and magnified motion of a tip of a rigid distal end of a phacoemulsification probe (that has an aspiration inlet and an irrigation outlet). The aspiration inlet and irrigation outlet of the tool are located in the same locations in the model tool and in the genuine tool, so they can be moved very accurately in the patient's eye as the physician performs the simulated phacoemulsification procedure on the enlarged eye model.

In another embodiment, to facilitate the mimicking motion with a single robot arm, both the model tool, and the genuine eye surgery tool, are position tracked. In an embodiment, a single robotic arm mimics a model tool that is hand-held (i.e., manually held in space by the physician). To this end, magnetic sensors are disposed both on the model tool and the actual eye surgery tool. A closed loop control circuitry uses signals from the two to perform the mimicked motions. Using registration and scaling as required, the loosened arm position and direction are tracked and mirrored (while scaling down the movements) to the robotic arm which holds the eye surgery tool.

System Description

FIG. 1 is a schematic, pictorial view of a robotic phacoemulsification apparatus 10 comprising a robotically held position-trackable mimicking phacoemulsification probe 12, in accordance with an embodiment of the present invention. FIG. 1 is brought by way of example of an eye surgery, where in general, element 12 can be any eye surgery tool used in performing the relevant eye surgery.

In the shown embodiment, system 10 comprises a magnetic-sensing subsystem 101 to estimate, during a phacoemulsification procedure, positions and directions of (i) a rigid distal end 137 of the hand-held model surgical tool 135, that physician 45 operates on the enlarged eye model 66, and (ii) phacoemulsification probe 12 coupled with robotic arm 55. An aspiration inlet 116 and irrigation outlet 156 of a mimicking rigid distal end 15 follow, with proper magnification factor, the motion of rigid distal end 137 of surgical tool 135. In the shown embodiment, eye model 66 is projected with a 3D image (not shown) of the actual patient eye that is acquired in real time using a 3D camera 70. The projected image enables the physician who is viewing eye model 66 to direct probe 12 at particles that need to be emulsified.

To facilitate scaled mimicked motion, apparatus 10 comprises a robotic arm 55 mounted on a fixed base 102 (e.g., suspended from a ceiling). Rigid distal end 15 of a phacoemulsification tool 12 is coupled with robotic arm 55, the distal end comprising an aspiration channel 16 and an irrigation channel 56 (which can be coaxial or side-by-side). As inset 25 shows, aspiration channel 16 includes aspiration inlet 116, and irrigation channel 56 includes irrigation outlet 156, both at a distal tip (15) of phacoemulsification probe 12, from which cataract fragments of a lens 18 of an eye 20 of a patient 19 are aspirated, and into which replenishment irrigation fluid flows, respectively.

In the shown embodiment, console 28 comprises a piezoelectric drive module 30, which is coupled, using electrical wiring running in a cable 33, with a piezoelectric crystal inside phacoemulsification probe 12. Drive module 30 is controlled by a processor 38 to adjust an ultrasound (US) power and/or duration and/or frequency.

During the phacoemulsification procedure, a pumping subsystem 24 comprised in a console 28 pumps irrigation fluid from an irrigation reservoir (not shown) to irrigation outlet 156 to irrigate the eye 20. The fluid is pumped via a tubing line 43 running from the console 28 to phacoemulsification probe 12. Eye fluid and waste matter (e.g., emulsified parts of the cataract) are aspirated via aspiration inlet 116 to a collection receptacle (not shown) by a pumping subsystem 26 also comprised in console 28 and using a tubing line 46 running from phacoemulsification probe 12 to console 28. An electrical cable 41 running from console 28 feeds power to probe 12. A set of cables/tubes, collectively numbered 31, can provide signals and/or power and/or fluid communication, if required, to model surgical tool 135 for performing a realistic procedure on enlarged eye model 66. However, the eye model can be such that it requires only to move the model tool inside the eye model, without the tool performing any other action.

To enable closed-loop controlled mimicking motion, patient 19 is placed in a magnetic-field generated by a pad containing magnetic-field generators (e.g., coils) 120, which are driven by unit 30 via a cable 33. The magnetic fields generated by coils 120 generate position signals in magnetic sensors 111 and 110. The signals from sensors 111 and 110 are then provided, for example, via interface circuits 32, as corresponding electrical inputs, to processor 38 to calculate the separate position and direction of rigid distal end 137 and mimicking rigid distal end 15, to enable the above mentioned "independent" (i.e., with feedback not from the robot itself) closed-loop control of the tool 12 motion in the patient's eye.

The method of position/direction sensing using external magnetic fields and magnetic sensor is implemented in various medical applications, for example, in the CARTO™ system, produced by Biosense-Webster, and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

While the eye model is seen in the vicinity of robot arm 55, in practice the tracking system can, mutatis mutandis, be engineered to track distal ends 15 and 137 that are further separated from each other. For example, the eye model may be located and tracked on a table while the physician is seated while performing the actions with tool 135. To this end, the magnetic tracking system comprises one or more separate pads.

Processor 38 presents results of the cataract removal procedure on display 36. Processor 38 may receive user-based commands via a user interface 40, which may include setting or adjusting an irrigation rate and/or aspiration rate. User interface 40 may be combined with a touch screen graphical user interface of display 36.

Some or all of the functions of processor 38 may be combined in a single physical component or, alternatively, implemented using multiple physical components. These physical components may comprise hard-wired or programmable devices, or a combination of the two. In some embodiments, at least some of the functions of processor 38 may be carried out by suitable software stored in a memory 35 (as shown in FIG. 1). This software may be downloaded to a device in electronic form, over a network, for example. Alternatively, or additionally, the software may be stored in tangible, non-transitory computer-readable storage media, such as optical, magnetic, or electronic memory.

The apparatus shown in FIG. 1 may include further elements, which are omitted for clarity of presentation. For example, physician 45 may further hold a control handle from which the physician can, for example, abort the automatic procedure. For example, the physician may command robotic arm 55 to disengage probe 12 from eye 20. As another example, physician 45 may operate a foot pedal (not shown) to control an emulsification power of probe 12.

Physician 45 may use other surgical tools and/or apply medications, which are also not shown in order to maintain clarity and simplicity of presentation. While rigid distal end 15 is shown straight, it may be curved or bent. While the shown embodiment uses a robotic arm having six degrees of freedom, the number of degrees of freedom may vary with design, typically with a minimum of three (e.g., to point at a solid angle direction and vary depth). In another embodiment, more than one robotic arm coupled with a respective mimicking tool, and more than one corresponding hand-held model surgical tool 135, may be used at the same time. For example, a system having both (1) a mimicking phacoemulsification tool 12 and corresponding hand-held model surgical tool; and (2) a mimicking tool for maneuvering lens material in the eye and a corresponding hand-held model tool.

Figure 2:
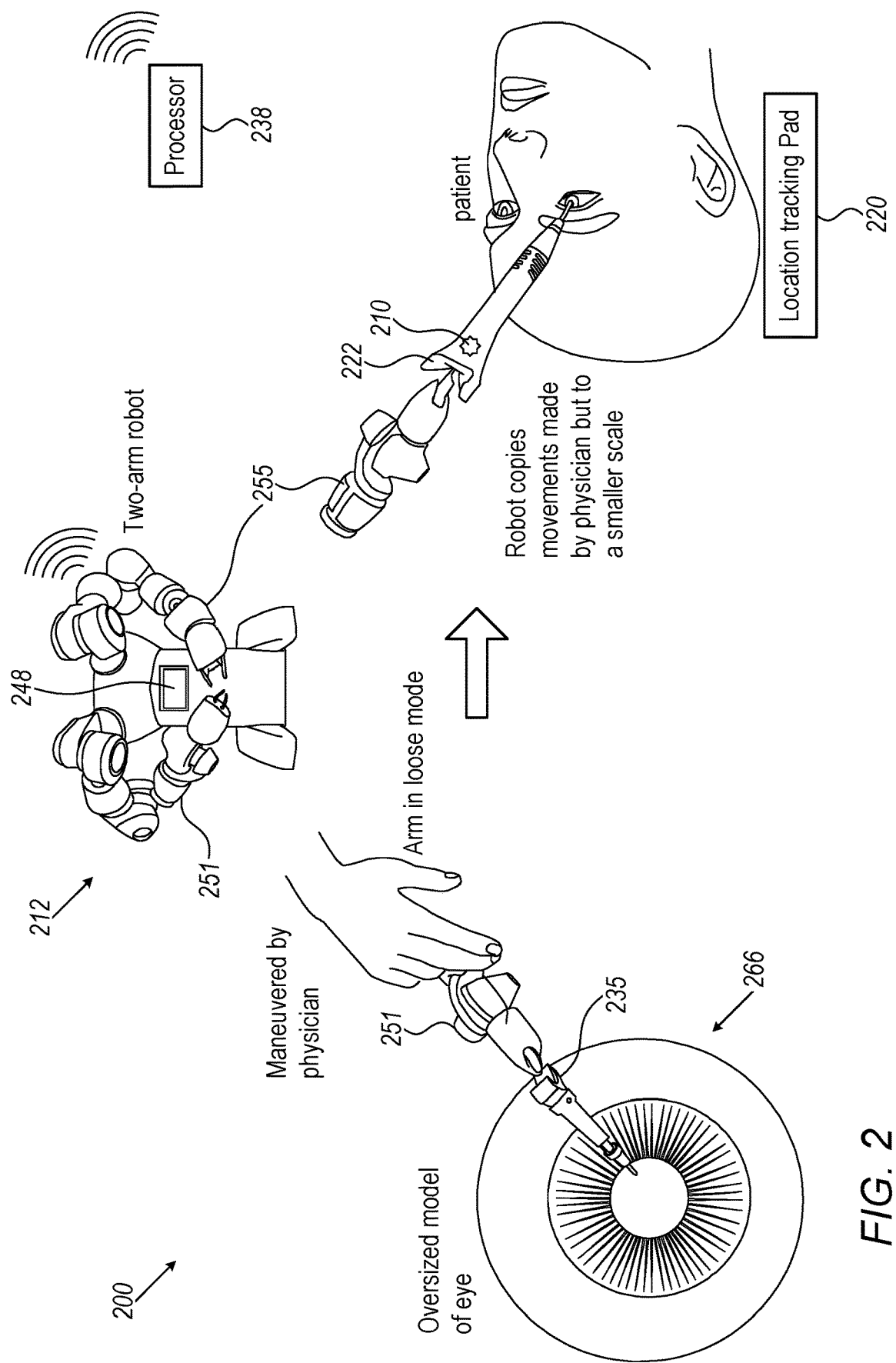
FIG. 2 is a schematic, pictorial view of a position-trackable robotic phacoemulsification apparatus comprising a robot with loose and mimicking robot arms, in accordance with an embodiment of the present invention.

Robotic Movement for Vision Care Surgery
Mimicking Probe Navigated by Magnetic Tracking FIG. 2 is a schematic, pictorial view of a position-trackable robotic phacoemulsification apparatus 200 comprising a robot 212 with loose (251) and mimicking (255) robot arms, in accordance with an embodiment of the present invention. FIG. 2 is brought by way of example of an eye surgery, where in general, apparatus 200 can be applied, mutatis mutandis, to use any eye surgery tool, including multiple tools, in performing the relevant eye surgery.

In the shown embodiment, a two-arm robot 212 (or two separate robotic arms which are registered with each other) is configured to perform cataract surgery. One robotic arm (251) is loosened so that it can be maneuvered by the physician (the shown hand). Loosened arm 251 is coupled with a model surgical (e.g., phacoemulsification) tool 235. The second robotic arm (255) is coupled with a genuine phacoemulsification probe 222 that is placed in proximity to the eye of a patient. As seen, probe 222 is disposed with a magnetic location sensor 210, which can be, for example, either a dual-axis sensor (DAS) or triple-axis sensor (TAS), configured to track at least a position and a direction in space. The movements of the genuine phacoemulsification probe 222 are tracked using a location tracking pad 220 (e.g., emitting alternating magnetic fields). Pad 220 may be placed in the vicinity of the patient (as shown), assuming that the head is secured, around the neck of the patient, or placed around the patient's head. The coordinate systems of the robot, the patient, robot and the magnetic tracking system are all registered one with the other using a processor 238 of the apparatus 200. Processor 238 can be wirelessly connected to the robot to exchange control signals.

The physician moves model surgical tools 235 using loosened arm 251 to perform a cataract procedure on an oversized model eye 266. The movements of the loosened arm are tracked by a controller 248 comprised in robot 212 and mirrored (while scaling down the movements) to the second robotic arm 255 which holds the mimicking surgical tool, e.g., genuine phacoemulsification probe 222 and performs the surgical procedure on the eye of the patient based on the movements of the physician. In this way, large movements of the physician may be translated to small movements of the probe to perform a very accurate cataract procedure.

The example focused US transmitter shown in FIG. 2 is chosen purely for the sake of conceptual clarity. For example, processor 238 may be integrated with the robot.

Figure 3:
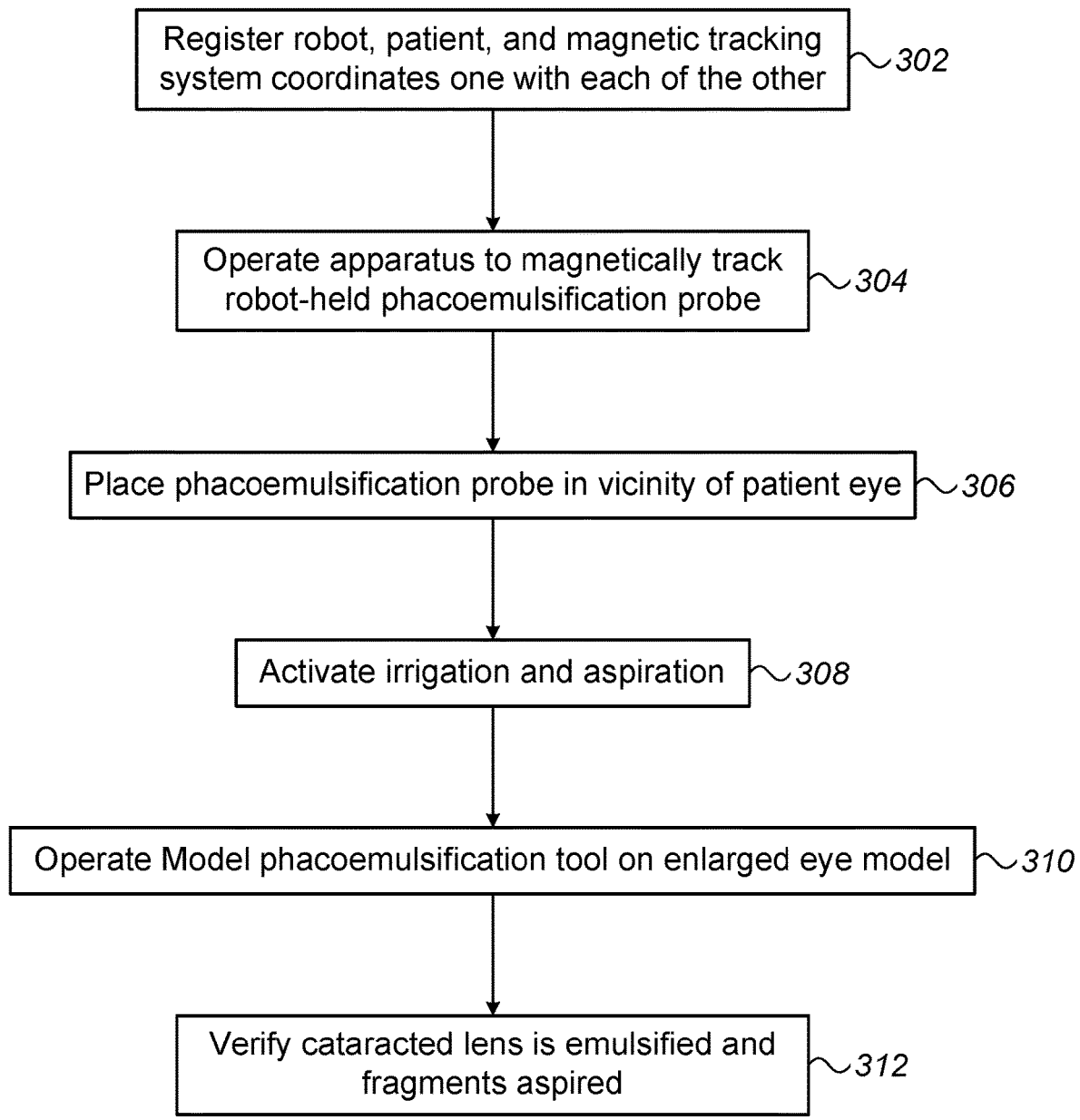
FIG. 3 is a flow chart schematically illustrating a method for phacoemulsification using the mimicking robot apparatus of FIG. 2, in accordance with an embodiment of the present invention.

FIG. 3 is a flow chart schematically illustrating a method for phacoemulsification using mimicking robot 212 apparatus 200 of FIG. 2, in accordance with an embodiment of the present invention. FIG. 3 is brought by way of example of an eye surgery, where in general, the method described in FIG. 3 can be applied, mutatis mutandis, to use with any eye surgery apparatus (having any number of robotic arms coupled with an additional mimicking eye surgery tool and corresponding additional hand-held model surgical tool) to perform the relevant eye surgery.

The algorithm, according to the presented embodiment, carries out a process that begins with physician 45 operating apparatus 200 to have processor 238 perform registration of a coordinate system of the robot, the patient and the magnetic tracking system, one with the other, at a registration step 302.

Next, the physician operates apparatus 200 (e.g., processor 238) to start tracking the position and direction of phacoemulsification probe 222, at a magnetic tracking initiation step 304.

In a probe placement step 306, the physician places phacoemulsification probe 222 in the vicinity of the patient's eye.

Then, at an activation step 308, the physician activates irrigation and aspiration. Next, the physician operates (e.g., moves) the model surgical tool 251 on the enlarged eye model 266.

As the physician moves the model surgical tool, the mimicking robotic system operates the magnetically tracked probe 222 to perform the actual cataract surgery. In this process, the physician may verify, at a verification step 312, that the patient's cataracted lens is emulsified and fragments are aspirated as the physician advances with the eye model.

The example flow chart shown in FIG. 3 is chosen purely for the sake of conceptual clarity. For example, the steps involving the patient itself, such as the engagement of the patient with the magnetic tracing system pad, are omitted.

Although the embodiments described herein mainly address eye surgery systems, the methods and systems described herein can also be used in other robotic medical surgery systems.

It will be thus appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An eye surgery apparatus, comprising:
a model surgical tool configured to be maneuvered by a physician;
a robotic arm coupled with an eye surgery tool that is configured to be placed in proximity to an eye of a patient;
a tracking system configured to track movements of at least the model surgical tool relative to a physical eye model; and
a processor configured to:
receive signals representative of the tracked movements of the model surgical tool relative to the physical eye model from the tracking system; and
cause the robotic arm to perform a surgical procedure on the eye of the patient using the eye surgery tool based on the tracked movements of the model surgical tool.

2. The eye surgery apparatus according to claim 1, further comprising an additional robotic arm that is configured to hold the model surgical tool and to be maneuvered by the physician relative to the physical eye model.

3. The eye surgery apparatus according to claim 2, wherein the additional robotic arm is movable to enable the physician to place the model surgical tool in contact with the physical eye model.

4. The eye surgery apparatus according to claim 1, wherein the model surgical tool is manually held in space by the physician.

5. The eye surgery apparatus according to claim 1, further comprising a magnetic position-tracking sensor associated with the eye surgery tool, and wherein the tracking system is further configured to track movements of the eye surgery tool by tracking the magnetic position-tracking sensor.

6. The eye surgery apparatus according to claim 5, wherein the tracking system is further configured to track the movements of the model surgical tool by tracking a second magnetic position-tracking sensor associated with the model surgical tool.

7. The eye surgery apparatus according to claim 1, further comprising a magnetic position-tracking sensor associated with the model surgical tool, and wherein the tracking system is configured to track the movements of the model surgical tool based on position signals from the magnetic position-tracking sensor.

8. The eye surgery apparatus according to claim 7, wherein the magnetic position-tracking sensor comprises one selected from the group consisting of a dual-axis sensor (DAS) and a triple-axis sensor (TAS).

9. The eye surgery apparatus according to claim 1, wherein the tracking system comprises a magnetic tracking system comprising a pad, and wherein the pad comprises one or more magnetic-field generators and is placed in a vicinity of the patient.

10. The eye surgery apparatus according to claim 1, wherein the eye surgery tool comprises a phacoemulsification probe.

11. The eye surgery apparatus according to claim 1, further comprising an additional robotic arm coupled with an additional eye surgery tool, wherein the additional robotic arm is configured to enable the additional eye surgery tool move in response to movements of an additional model surgery tool.

12. The eye surgery apparatus according to claim 11, wherein the additional eye surgery tool is configured to move lens material in the eye.

13. The eye surgery apparatus according to claim 1, wherein the physical model eye is projected with a 3D image representative of the eye of the patient, wherein the 3D image is provided in real time.

14. An eye surgery method, comprising:
providing a model surgical tool to be maneuverable by a physician;
placing an eye surgery tool, coupled to a robotic arm, in proximity to an eye of a patient;
tracking movements of at least the model surgical tool relative to a physical eye model using a tracking system;
receiving, at a processor, signals representative of the tracked movements of the model surgical tool relative to the physical eye model from the tracking system; and
causing the robotic arm to perform a surgical procedure on the eye of the patient using the eye surgery tool based on the tracked movements of the model surgical tool.

15. The eye surgery method according to claim 14, further comprising moving an additional robotic arm, wherein the additional robotic arm includes the model surgical tool that is configured to be maneuvered by the physician relative to the physical eye model.

16. The eye surgery method according to claim 15, wherein the additional robotic arm is moveable to enable the physician to place the model surgical tool in contact with the physical eye model.

17. The eye surgery method according to claim 14, wherein the model surgical tool is manually held in space by the physician.

18. The eye surgery method according to claim 14, further comprising, tracking the movements of the eye surgery tool by tracking a magnetic position-tracking sensor associated with the eye surgery tool.

19. The eye surgery method according to claim 18, wherein tracking the movements of the model surgical tool comprises tracking a second magnetic position-tracking sensor associated with the model surgical tool.

20. The eye surgery method according to claim 14, wherein tracking the movements of the model surgical tool comprises tracking a magnetic position-tracking sensor associated with the model surgical tool.

21. The eye surgery method according to claim 20, wherein the magnetic position-tracking sensor comprises one selected from the group consisting of a dual-axis sensor (DAS) and a triple-axis sensor (TAS).

22. The eye surgery method according to claim 14, wherein the tracking system comprises a magnetic tracking system comprising a pad, and wherein the pad comprises one or more magnetic-field generators and is placed in a vicinity of the patient.

23. The eye surgery method according to claim 14, wherein the eye surgery tool comprises a phacoemulsification probe.

24. The eye surgery method according to claim 14, further comprising causing an additional eye surgery tool, coupled to an additional robotic arm, to move in response to movement of an additional model surgery tool.

25. The eye surgery method according to claim 24, wherein the additional eye surgery tool is configured to move lens material in the eye.

26. The eye surgery method according to claim 14, further comprising projecting a 3D image of the eye of the patient onto the physical model eye, wherein the 3D image is provided in real time.

* * * * *